(12) United States Patent
Kysilka et al.

(10) Patent No.: US 6,589,988 B1
(45) Date of Patent: Jul. 8, 2003

(54) PHARMACEUTICAL COMPOSITION WITH ANTITUMOR ACTIVITY ON THE BASIS OF CARBOPLATIN

(75) Inventors: VladimíR Kysilka, Brno (CZ); Libuše Zatloukalová, Brno (CZ); Miroslav Maleček, Brno (CZ); Ronald Gust, Schierling (DE)

(73) Assignee: Pliva-Lachema, a.s., Brno (CZ)

( * ) Notice: Subject to any disclaimer, the term of this patent is extended or adjusted under 35 U.S.C. 154(b) by 0 days.

(21) Appl. No.: 09/762,458

(22) PCT Filed: Aug. 10, 1999

(86) PCT No.: PCT/CZ99/00028

§ 371 (c)(1),
(2), (4) Date: Jun. 11, 2001

(87) PCT Pub. No.: WO00/09097

PCT Pub. Date: Feb. 24, 2000

(30) Foreign Application Priority Data

Aug. 14, 1998 (CS) .............................................. 2588-98

(51) Int. Cl.$^7$ ................................................. C08K 3/34
(52) U.S. Cl. ...................................................... 514/492
(58) Field of Search ......................................... 574/492

(56) References Cited

FOREIGN PATENT DOCUMENTS

WO       20956   *   8/1995

* cited by examiner

*Primary Examiner*—Sheela Huff
(74) *Attorney, Agent, or Firm*—Notaro & Michalos P.C.

(57) ABSTRACT

The invention concerns a pharmaceutical composition with antitumor activity based on carboplatin, comprising an aqueous solution of carboplatin with the carboplatin content from 1 to 20 mg·ml$^{-1}$. The pharmaceutical composition contains, immediately after its preparation, less than 0.1% by weight 1,1-cyclobutanedicarboxylic acid ("CBDCA") and/or salt thereof, based on the weight of the present carboplatin.

1 Claim, No Drawings

PHARMACEUTICAL COMPOSITION WITH ANTITUMOR ACTIVITY ON THE BASIS OF CARBOPLATIN

FIELD OF THE INVENTION

The invention concerns a pharmaceutical composition with antitumor activity based on carboplatin and comprising an aqueous solution of carboplatin with a carboplatin content of from 1 to 20 mg/ml.

PRIOR ART

Carboplatin (cis-diammin-1,1-cyclobutanedicarboxylatoplatinum(II) complex) is an active substance which is useful in treatment of tumors. This platinum cytostatic agent was introduced into medicinal practice in 1986 in a form of freeze dried powder for injection containing mannitol as a pharmaceutically acceptable trituration agent. Although the freeze dried product is stable, production of dry injections by freeze drying consumes much time and energy. The disadvantage in application of the lyophilization form of carboplatin is in cumbersome preparation of the carboplatin solution for infusion application; there exists, moreover, a certain risk for personnel based on possible interaction of carboplatin with DNA leading to chromosomal aberations. Namely these disadvantages motivated the efforts to prepare a liquid medicinal form of carboplatin which, due to limited manipulation, would lead to a decrease of risk of contamination of the environment and the medical personnel.

The basic problem in production of a liquid drug form of carboplatin is based on the fact that solutions of carboplatin in water or certain water solutions are stable and therapeutically useful only in a time interval of several hours or days. After this time, unwanted highly toxic aquacomplexes and/or other toxic substances are being formed in big extent in solutions of carboplatin. Solving the stability of carboplatin in aqueous solutions is therefore crucial for commercial application of aqueous solutions of carboplatin.

European patent document EP 334 551 describes a liquid drug form of carboplatin which is stabilized by addition of mannitol and benzyl alcohol which serve herein as conservation agents. The disadvantage of this way of stabilization is in that it does not solve the long-term stability of aqueous solutions of carboplatin. The European patent document EP 401896 describes an aqueous drug form of carboplatin which is stabilized by a buffer maintaining the pH value of the aqueous solution of carboplatin in the range of 2–6. In the patent document CZ 281349, there is described an aqueous drug form of carboplatin which is stabilized by presence of from 0.01 to 0.5 mg/ml of 1,1-cyclobutanedicarboxylic acid and/or its ammonium, sodium or potassium salt. The patent document EP 642 792 describes an aqueous drug form of carboplatin which is stabilized by presence of 0.25 to 4 mg/ml of 1,1-cyclobutanedicarboxylic acid or its alkaline metal salt maintaining the pH of the solution in the range of from 4 to 7. Finally, the patent document PCT WO95-20956 describes an aqueous drug form of carboplatin the stability of which is assured by the pH value of the carboplatin solution in the range of from 2.5 to 7 and by the presence of 1,1-cyclobutanedicarboxylic acid and/or its sodium, potassium or ammonium salt, whereby the obligatory part of this solution is that at least $1.10^{-4}$ mg/ml of these compounds are present in a form of mono- or bivalent anion.

It is apparent from the hereinabove that there exists a conviction among persons skilled in this art that the presence of 1,1-cyclobutanedicarboxylic acid and/or its above cited salts is absolutely necessary for to attain certain acceptable stability of aqueous solutions of carboplatin.

After a thorough study of kinetics of carboplatin hydrolysis in aqueous solutions, this professional prejudice specified above has been now overcome by a new and surprising finding which may be summarized in a statement that the presence of a whatever acid facilitates the hydrolysis of carboplatin by an electrophilic attack of carboxylic ligands of carboplatin. Similarly, any nucleophilic compound which possesses stronger nucleophilicity than water may decrease the stability of carboplatin due to a substitution of the carboxylate ligand of carboplatin. Thus, any presence of a buffer including the 1,1-cyclobutanedicarboxylic acid and/or its conjugated base in a form of a salt will, contrary to expectations, decrease the stability of carboplatin in an aqueous solution. In variance with the so far accepted conviction, the most stable aqueous drug form of carboplatin is an aqueous solution of a highly pure carboplatin in a sterile water for injection, without any other components, namely nucleophilic compounds or acids.

DESCRIPTION OF THE INVENTION

An object of the present invention is thus a pharmaceutical composition with antitumor activity based on carboplatin and comprising an aqueous solution of carboplatin with the carboplatin content from 1 to 20 mg·ml$^{-1}$, characterized in that it contains immediately after its preparation less than 0.1% by weight 1,1-cyclobutanedicarboxylic acid ("CBDCA") and/or salt thereof, based on the weight of the present carboplatin.

Presumed mechanism of decomposition of carboplatin which is analogical to the disclosed mechanism of hydratation of cisplatin (Cheung Y. W., Cradock J. C., Vishnuvajjala B. B., Flora K. P., Am. J. Hosp. Pharm., 1987,44,124) is a two-step hydrolysis to mono- and diaquacomplexes of platinum of the formulas I and II:

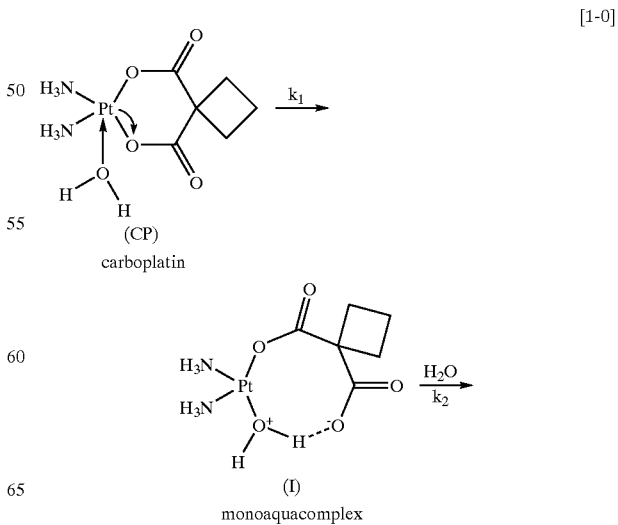

(CP) carboplatin (I) monoaquacomplex

-continued

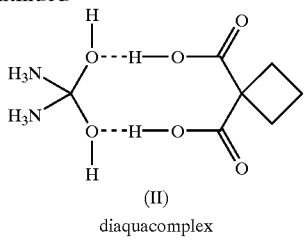

(II)
diaquacomplex

The first step of decomposition of carboplatin in an aqueous solution according to the equation /1-0/ which causes the instability can be further generalised by the equation /1-1/:

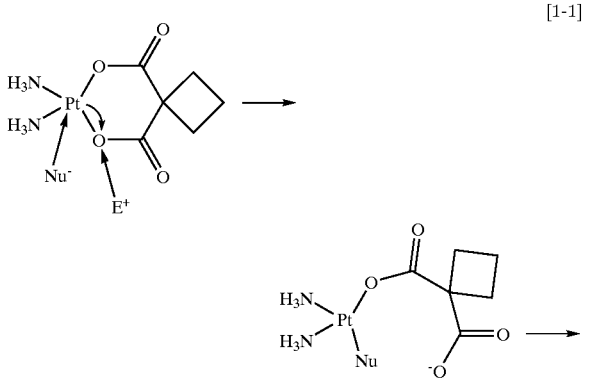

[1-1]

It is apparent from the equations /1-0/ and /1-1/ that each acid or each nucleophilic compound which is a stronger nucleophile than water will decrease the stability of carboplatin by a mechanism of substitution of the carboxylate ligand of carboplatin. Although this presumption from the equation /1-1/ is logical, it is in the contrary to all the so far published statements. For to support the overcoming of the above formulated professional prejudice by evidences, there were collected and worked up data from stability studies of liquid carboplatin injections which differed in content of 1,1-cyclobutanecarboxylic acid and/or their salts.

The rate of hydrolysis of carboplatin to a monoaquacomplex of the formula (1) has been presumed to be of the first order in relation to carboplatin concentration and independent to water concentration:

$$r_{CP} = -\frac{dc_{CP}}{dt} = k_0 \cdot c_{H2O} \cdot c_{CP} = k_1 \cdot c_{CP} - \frac{dc_{CP}}{c_{CP}} = k_1 \cdot dt, \quad /1\text{-}2/$$

which may be integrated to:

$$\ln\frac{c_{CP}}{c_{CP0}} = -k_1 \cdot t, \text{ which may be laid out as:} \quad /1\text{-}3/$$

$$\ln(1-x) = -k_1 \cdot t$$

Dependences on concentration according to equations /1-2/ and /1-3/ were evaluated by linear regression and the rate constant and/or the reaction rate of the carboplatin decomposition have been calculated.

Study of the decomposition rate of carboplatin in dependence on the concentration of 1,1-cyclobutanedicarboxylic acid.

Mean starting concentration of carboplatin was 10.0 mg·ml$^{-1}$. Starting concentrations of 1,1-cyclobutanedicarboxylic acid were 0.017, 0.129, 1.189 and 14.804 mg·ml$^{-1}$. The temperature and relative humidity during storage was 25° C./60% and 35° C./60%. The vials with samples were stored stopper upright.

The decrease of carboplatin content was calculated as a difference of carboplatin content between a reference and measured sample. The concentration data were evaluated according to equation /1-2/, whereby, due to a good linear relation, the data were evaluated by linear regression.

The calculated decomposition rates of carboplatin (r, /mol·m$^{-3}$·s$^{-1}$/) are summarised in the table:

| concentration of 1,1-cyclobutanedicarbo-xylic acid (mg · ml$^{-1}$) | Storage temperature | |
|---|---|---|
| | 25° C. | 35° C. |
| 0.017 | 4.0 · 10$^{-9}$ | 4.9 · 10$^{-8}$ |
| 0.129 | 4.0 · 10$^{-9}$ | 5.1 · 10$^{-8}$ |
| 1.189 | 9.4 · 10$^{-9}$ | 7.3 · 10$^{-8}$ |
| 14.804 | 2.2 · 10$^{-8}$ | 1.7 · 10$^{-7}$ |

The following concentration dependences of reaction rates were obtained at storage temperatures 25 C and 35 C:

$$r_{25} = 5.2 \cdot 10^{-9} + 1.7 \cdot 10^{-10} \cdot C_{CBDCA} /\text{mol·m}^{-3}\cdot\text{s}^{-1}/ \quad /1\text{-}4/$$

$$r_{35} = 5.4 \cdot 10^{-8} + 1.2 \cdot 10^{-9} \cdot C_{CBDCA} /\text{mol·m}^{-3}\cdot\text{s}^{-1}/ \quad /1\text{-}5/$$

(CBDCA=1,1-cyclobutanedicarboxylic acid)

After evaluation of Arrhenius equation, the activation energy $E_A$ was calculated:

$$E_A = 190\,000 \text{ J·mol}^{-1} \quad /1\text{-}6/$$

The calculated value shows a strong dependence of the decomposition rate of carboplatin on the temperature. For the reference temperature of 35° C., at which the best determination coefficient has been obtained ($R^2$=0.99), the following dependence of the decomposition rate of carboplatin on the concentration of the present 1,1-cyclobutanedicarboxylic acid and on the temperature may be obtained from the equations /1-5/ and /1-6/:

$$r = (5.4 \cdot 10^{-8} + 1.2 \cdot 10^{-9} \cdot c_{CBDCA}) \cdot \exp\left[74.2 \cdot \frac{T-308}{T}\right] \quad /1\text{-}7/$$

wherein r is expressed in mol·m$^{-3}$·s$^{-1}$ and $C_{CBDCA}$ is expressed in mol·m$^{-3}$.

Based on the equation /1-7/, it is possible to calculate decomposition rates of carboplatin at the temperature of 25° C. and for different concentrations of 1,1-cyclobutanedicarboxylic acid:
a) concentration of 1,1-cyclobutanedicarboxylic acid is 0.005 mg/ml (the concentration in the range according to the present invention):
r=4.48·10$^{-9}$ mol·m$^{-3}$·s$^{-1}$,
b) concentration of 1,1-cyclobutanedicarboxylic acid is 0.150 mg/ml (a concentration in the commercially produced carboplatin drug form Ribocarbol L):
r=4.58·10$^{-9}$ mol·m$^{-3}$·s$^{-1}$, (rate increase 2.2%)
c) concentration of 1,1-cyclobutanedicarboxylic acid is 0.250 mg/ml (a lower concentration limit in an aqueous drug form of carboplatin according to EP 642 792):
r=4.65·10$^{-9}$ mol·m$^{-3}$·s$^{-1}$, (rate increase 4%).

It is apparent from the above disclosed data that the rate of decomposition of carboplatin in an aqueous solution depends, according to the obtained equation /1-7/, negatively on the amount of the present 1,1-cyclobutanedicarboxylic acid and/or its salts and strongly negatively on the storage temperature. The rate constant k in 0.1 M phosphate buffer at the temperature of 37° C. is approximately 200 times higher than in $1.4 \cdot 10^{-4}$M CBDCA-buffer at the temperature of 40° C. An enhancement of temperature of 10° C. causes approximately tenfold increase of the decomposition rate of carboplatin, thus indicating a strong dependence of carboplatin stability in an aqueous solution on the temperature. It is apparent from the data obtained in long-term stability studies that the most stable liquid drug form of carboplatin is a solution of a pure carboplatin in water with minimal content of other impurities, namely acids or nucleophiles. The content of 1,1-cyclobutanedicarboxylic acid and its salts, eventually other buffering agents or nucleophilic compounds, in the aqueous drug form of carboplatin should be lower than 0.1% by weight of the carboplatin present, i.e. lower than 0.01 mg/ml for the carboplatin concentration of 10 mg/ml. At prolonged storage times (up to several years) or at enhanced temperatures, yellow colouration appears in the liquid drug form of carboplatin, probably due to disproportionation of carboplatin into Pt (IV) and Pt(0) complexes. For to avoid this disproportionation, the liquid drug form of carboplatin should be stored under exclusion of light, eventually in vials made from amber glass of proper hydrolytic class.

EXAMPLES

Example 1

Under conditions of GMP, a sterile aqueous solution of carboplatin with the carboplatin concentration of 10.03 mg/ml was prepared from the carboplatin substance having the purity of 99.85% and containing 0.05% by weight of 1,1-cyclobutanedicarboxylic acid and 0.05% by weight of water. The solution having pH value of 6.3 was ultrafiltered under aseptic conditions through a filter with porosity of 0.2 μm and then refilled by 5 ml portions into vials made from glass of the first hydrolytic class which were closed by teflon-coated rubber stoppers with aluminium caps. Atmospheric air formed the gaseous environment above the solution. The prepared compositions were subjected to a stability study at 25° C. and 60% relative humidity under exclusion of light. The vials were stored stopper upright. The contents of carboplatin and 1,1-cyclobutanedicarboxylic acid were monitored by high performance liquid chromatography and evaluated in comparison with an external reference standard. After 36 months, the pharmaceutical composition exhibited 9.85 mg/ml of carboplatin, i.e. the decrease of content of the active substance was 1.8%.

Example 2

Under conditions of GMP, a sterile aqueous solution of carboplatin with the carboplatin concentration of 9.99 mg/ml was prepared from the carboplatin substance having the purity of 99.82% and containing 0.08% by weight of 1,1-cyclobutanedicarboxylic acid and 0.07% by weight of water. The resulted pharmaceutical composition having pH value of 6.2 was refilled by 15 ml portions. The subsequent procedure was identical with that of the Example 1. After 36 months, the pharmaceutical composition exhibited 9.80 mg/ml of carboplatin, i.e. the decrease of content of the active substance was 1.9%.

Example 3

Under conditions of GMP, a sterile aqueous solution of carboplatin with the carboplatin concentration of 10.02 mg/ml was prepared from the carboplatin substance having the purity of 99.86% and containing 0.03% by weight of 1,1-cyclobutanedicarboxylic acid and 0.10% by weight of water. The resulted pharmaceutical composition having pH value of 6.3 was refilled by 45 ml portions. The subsequent procedure was identical with that of the Example 1. After 36 months, the pharmaceutical composition exhibited 9.84 mg/ml of carboplatin, i.e. the decrease of content of the active substance was 1.8%.

Example 4 (Comparative Example)

Under conditions of GMP, a sterile aqueous solution of carboplatin with the carboplatin concentration of 10.03 mg/ml and with the concentration of 1,1-cyclobutanedicarboxylic acid of 0.25 mg/ml (i.e. minimal stabilizing concentration according to EP 642 792) was prepared from the carboplatin substance having the purity of 99.85% and containing 0.05% by weight of 1,1-cyclobutanedicarboxylic acid and 0.05% by weight of water, and from the substance of 1,1-cyclobutanedicarboxylic acid having the purity of 99.7% and containing 0.12% by weight of water. The pH value was adjusted to 6.0 by means of NaOH. The subsequent procedure was identical with that of the Example 1. After 36 months, the pharmaceutical composition exhibited 9.83 mg/ml of carboplatin, i.e. the decrease of content of the active substance was 2.0%.

Example 5 (Comparative Example)

Under conditions of GMP, a sterile aqueous solution of carboplatin with the carboplatin concentration of 9.95 mg/ml and with the concentration of 1,1-cyclobutanedicarboxylic acid of 1.19 mg/ml (i.e. median value from the interval of stabilizing concentrations according to EP 642 792) was prepared from the carboplatin substance having the purity of 99.85% and containing 0.05% by weight of 1,1-cyclobutanedicarboxylic acid and 0.05% by weight of water, and from the substance of 1,1-cyclobutanedicarboxylic acid having the purity of 99.7% and containing 0.12% by weight of water. The pH value of the solution was 5.7. The subsequent procedure was identical with that of the Example 1. After 36 months, the pharmaceutical composition exhibited 9.73 mg/ml of carboplatin, i.e. the decrease of content of the active substance was 2.2%.

Example 6 (Comparative Example)

Under conditions of GMP, a sterile aqueous solution of carboplatin with the carboplatin concentration of 9.73 mg/ml and with the concentration of 1,1-cyclobutanedicarboxylic acid of 14.80 mg/ml was prepared from the carboplatin substance having the purity of 99.85% and containing 0.05% by weight of 1,1-cyclobutanedicarboxylic acid and 0.05% by weight of water, and from the substance of 1,1-cyclobutanedicarboxylic acid having the purity of 99.7% and containing 0.12% by weight of water. The pH value of the solution was 5.5. The subsequent procedure was identical with that of the Example 1. After 36 months, the pharmaceutical composition exhibited 8.94 mg/ml of carboplatin, i.e. the decrease of content of the active substance was 8.1%.

The abbreviation GMP as used throughout the Examples is an abbreviated expression of commonly used technical term, Good Manufacturing Practice, which characterises that a set of specific rules and conditions required in pharmaceutical practice was met.

What is claimed is:

1. A pharmaceutical composition with antitumor activity based on carboplatin comprising an aqueous solution of carboplatin with a carboplatin content from 1 to 20 mg·ml$^{-1}$, and containing immediately after its preparation less than 0.1% by weight 1,1-cyclobutanedicarboxylic acid and/or a salt thereof that is exclusively formed from carboplatin production.

* * * * *